(12) United States Patent
Yamamoto et al.

(10) Patent No.: US 7,846,969 B2
(45) Date of Patent: Dec. 7, 2010

(54) CERAMIDE EMULSIONS

(75) Inventors: Yumiko Yamamoto, Tokyo (JP); Masanori Tanahashi, Tokyo (JP)

(73) Assignee: Kao Corporation, Tokyo (JP)

(*) Notice: Subject to any disclaimer, the term of this patent is extended or adjusted under 35 U.S.C. 154(b) by 963 days.

(21) Appl. No.: 10/498,112

(22) PCT Filed: Dec. 10, 2002

(86) PCT No.: PCT/JP02/12899

§ 371 (c)(1),
(2), (4) Date: Mar. 9, 2005

(87) PCT Pub. No.: WO03/049709

PCT Pub. Date: Jun. 19, 2003

(65) Prior Publication Data

US 2005/0152865 A1    Jul. 14, 2005

(30) Foreign Application Priority Data

Dec. 10, 2001   (JP)   ............................. 2001-376412
Dec. 10, 2001   (JP)   ............................. 2001-376413

(51) Int. Cl.
*A61K 31/225*   (2006.01)
*A61K 8/02*   (2006.01)
*A01N 37/06*   (2006.01)

(52) U.S. Cl. ...................... 514/547; 424/401
(58) Field of Classification Search ................. 424/401; 514/547

See application file for complete search history.

(56) References Cited

U.S. PATENT DOCUMENTS

| | | | |
|---|---|---|---|
| 5,578,641 A * | 11/1996 | Jackson et al. | ............... 514/547 |
| 5,635,536 A | 6/1997 | Lyons | |
| 5,641,495 A | 6/1997 | Jokura et al. | |
| 5,677,341 A | 10/1997 | Lyons | |
| 5,882,665 A | 3/1999 | Meyers et al. | |
| 5,958,426 A * | 9/1999 | Moreau et al. | ........... 424/283.1 |

FOREIGN PATENT DOCUMENTS

| | | |
|---|---|---|
| CA | 2 281 430 | 12/2000 |
| DE | 197 51 550 A1 | 7/1999 |
| EP | 0 940 140 A1 | 9/1999 |
| FR | 2794366 | 12/2000 |
| JP | 63-192703 | 8/1988 |
| JP | 10-510267 | 10/1998 |
| JP | 2001-39859 | 2/2001 |
| JP | 2001-48721 | 2/2001 |
| JP | 2001-122734 | 5/2001 |
| JP | 2001-181169 | 7/2001 |
| JP | 2001-199872 | 7/2001 |
| JP | 2001-233754 | 8/2001 |
| JP | 2002-212100 | 7/2002 |
| WO | WO 99/29293 | 6/1999 |
| WO | WO 01/70235 A1 | 9/2001 |

OTHER PUBLICATIONS

Dictionary of Biochemistry, Published by Tokyo Kagaku Dozin Co. Ltd., Ver. 3, 1998, pp. 745-746, 784 (with Partial English Translation).
U.S. Appl. No. 11/183,965, filed Jul. 19, 2005, Kawakami et al.
Genji Imokawa, et al., The Journal of Investigative Dermatology, vol. 84, No. 4, pp. 282-284 1985.
Genji Imokawa, The Journal of Investigative Dermatology, vol. 87, No. 6, pp. 758-761 1986.
Philip W. Wertz, et al., Journal of Lipid Research, vol. 24, pp. 759-765 1983.
Philip W. Wertz, et al., The Journal of Investigative Dermatology, vol. 94, No. 2, pp. 159-161 1990.

* cited by examiner

*Primary Examiner*—Frederick Krass
*Assistant Examiner*—Benjamin Packard
(74) *Attorney, Agent, or Firm*—Oblon, Spivak, McClelland, Maier & Neustadt, L.L.P.

(57) ABSTRACT

A process for the production of a stabilized ceramide emulsion by adding one or more ceramides of Formula (2) to one or more sphingosines of Formula (1), and then adding an acidic compound and water to form one or more sphingosine salts, wherein the sphingosine salts emulsify the ceramides to form the emulsion.

11 Claims, No Drawings

CERAMIDE EMULSIONS

FIELD OF INVENTION

The present invention relates to a ceramide emulsion (an emulsion of ceramides) which has a good storage stability and is excellent in a rough skin-improving effect and a skin barrier property and which has a high safety, and to a process for production of the same.

BACKGROUND OF THE INVENTION

A horny layer that forms the outermost layer of the skin has the functions of inhibiting penetration of substances from the outside and volatilization of moisture from the inside of the skin and of maintaining a flexibility and a smooth appearance of the skin by virtue of moisture held by the horny layer itself. The horny layer is constituted from horny cells, and a lipid called a horny intercellular lipid (hereinafter referred to as a horny ICL) forms a stratified structure between the spaces of the horny cells to fill up the spaces between the horny cells.

A ceramide accounting for about 50% of this horny ICL attracts attentions as an active ingredient for the skin reduced in moisture such as rough skin, dry skin or aged skin. Further, it is also known that the state of a horny layer reduced in a performance can be improved by externally supplementing a ceramide as a component for improving a horny layer performance (J. Invest. Dermatol., 84: 282 (1985) and J. Invest. Dermatol., 87: 758 (1986).

However, ceramides, including natural ceramides, are substances having a very high melting point and a strong crystallinity. Accordingly, a large amount of an oil and a surfactant has to be used in order to prepare a stable skin external preparation. As a result thereof, the properties of a skin external composition containing ceramides have been restricted, and therefore the use feeling has inevitably been further reduced.

SUMMARY OF THE INVENTION

The present inventors have found that emulsification of ceramides with sphingosines and a specific acid makes it possible to stably maintain the ceramides without crystallization to provide an emulsion of ceramides which is excellent in a storage stability.

The present invention provides a ceramide emulsion containing (A) sphingosines represented by Formula (1), (B) an acidic compound selected from inorganic acids and organic acids having a molecular weight of 200 or less and (C) ceramides represented by Formula (2) and not containing an acrylic acid polymer or a phospholipid, and a process for production thereof:

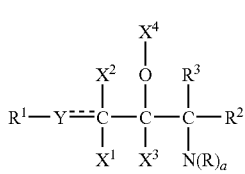
(1)

wherein $R^1$ represents a linear, branched or cyclic, saturated or unsaturated hydrocarbon group having 4 to 30 carbon atoms which may be (is optionally) substituted with a hydroxyl group, a carbonyl group or an amino group; Y represents a methylene group, a methine group or an oxygen atom; $X^1$, $X^2$ and $X^3$ each represent independently a hydrogen atom, a hydroxyl group or an acetoxy group, and $X^4$ represents a hydrogen atom, an acetyl group or a glyceryl group or, together with an adjacent oxygen atom, forms an oxo group, wherein when Y is a methine group, one of $X^1$ and $X^2$ is a hydrogen atom, and the other is not present, and when $X^4$ forms an oxo group, $X^3$ is not present; $R^2$ and $R^3$ each represent independently a hydrogen atom, a hydroxyl group, a hydroxymethyl group or an acetoxymethyl group; groups "R"s each are independently a hydrogen atom or an amidino group or each represents independently a linear or branched, saturated or unsaturated hydrocarbon group having in total 1 to 8 carbon atoms which may have a substituent selected from a hydroxyl group, a hydroxyalkoxy group, an alkoxy group and an acetoxy group; "a" represents a number of 2 or 3; and a bond represented by a "broken line and solid line" represents a single bond or a double bond;

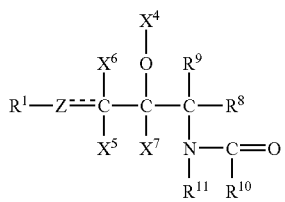
(2)

wherein $R^7$ represents a linear, branched or cyclic, saturated or unsaturated hydrocarbon group having 4 to 30 carbon atoms which may be substituted with a hydroxyl group, a carbonyl group or an amino group; Z represents a methylene group, a methine group or an oxygen atom; $X^5$, $X^6$ and $X^7$ each represent independently a hydrogen atom, a hydroxyl group or an acetoxy group, and $X^4$ represents a hydrogen atom, an acetyl group or a glyceryl group or, together with an adjacent oxygen atom, forms an oxo group, wherein when Z is a methine group, one of $X^5$ and $X^6$ is a hydrogen atom, and the other is not present, and when $X^4$ forms an oxo group, $X^7$ is not present; $R^8$ and $R^9$ each represent independently a hydrogen atom, a hydroxyl group, a hydroxymethyl group or an acetoxymethyl group; $R^{10}$ represents a linear, branched or cyclic, saturated or unsaturated hydrocarbon group having 5 to 60 carbon atoms which may be substituted with a hydroxyl group, a carbonyl group or an amino group and which may have an ether bond, an ester bond or an amide bond in a principal chain; $R^{11}$ represents a hydrogen atom or a linear or branched, saturated or unsaturated hydrocarbon group having in total 1 to 8 carbon atoms which may have a substituent selected from a hydroxyl group, a hydroxyalkoxy group, an alkoxy group and an acetoxy group; and a bond represented by a "broken line and solid line" represents a single bond or a double bond.

DETAILED DESCRIPTION OF THE INVENTION

The sphingosines of the component (A) used in the present invention are represented by Formula (1) described above, and $R^1$ in the formula is a linear, branched or cyclic, saturated or unsaturated hydrocarbon group having 4 to 30 carbon atoms which may be substituted with a hydroxyl group, a carbonyl group or an amino group, preferably having 7 to 22 carbon atoms which may be substituted with a hydroxyl group. More preferably, $R^1$ is a linear or branched alkyl group having 10 to 20 carbon atoms, or a linear or branched alkyl group having 10 to 20 carbon atoms and having a hydroxyl group at a Y side end, and when $R^1$ is a branched alkyl group, the branched alkyl group is preferably methyl-branched. Preferred $R^1$ are tridecyl, tetradecyl, pentadecyl, hexadecyl, 1-hydroxytridecyl, 1-hydroxypentadecyl, isohexadecyl and isostearyl groups.

Y represents any of a methylene group ($CH_2$), a methine group (CH) and an oxygen atom.

$X^1$, $X^2$ and $X^3$ each represent independently a hydrogen atom, a hydroxyl group or an acetoxy group, and $X^4$ represents a hydrogen atom, an acetyl group, a glyceryl group or a substituent forming an oxo group together with an adjacent oxygen atom. Preferred is a case in which zero to one of $X^1$, $X^2$ and $X^3$ is a hydroxyl group and the remainder is a hydrogen atom and $X^4$ is a hydrogen atom. When Y is a methine group, only one of $X^1$ and $X^2$ is a hydrogen atom, and the other is not present. When $X^4$ forms an oxo group, $X^3$ is not present.

$R^2$ and $R^3$ each represent independently a hydrogen atom, a hydroxyl group, a hydroxymethyl group or an acetoxymethyl group, and $R^3$ is preferably a hydrogen atom.

Further, "a" represents a number of 2 or 3. When a is 2, R represents $R^4$ and $R^5$, and when a is 3, R represents $R^4$, $R^5$ and $R^6$.

$R^4$, $R^5$ and $R^6$ each are independently a hydrogen atom or an amidino group or each represent independently a linear or branched, saturated or unsaturated hydrocarbon group having in total 1 to 8 carbon atoms which may have a substituent selected from a hydroxyl group, a hydroxyalkoxy group, an alkoxy group and an acetoxy group. In this respect, the hydroxyalkoxy group which can be a substituent of the hydrocarbon group is preferably a linear or branched hydroxyalkoxy group having 1 to 7 carbon atoms. Also, the alkoxy group is preferably a linear or branched alkoxy group having 1 to 7 carbon atoms. $R^4$, $R^5$ and $R^6$ include, for example, a hydrogen atom; linear or branched alkyl groups such as methyl, ethyl, propyl, 2-ethylhexyl and isopropyl; alkenyl groups such as vinyl and allyl; an amidino group; and hydrocarbon groups having in total 1 to 8 carbon atoms which have 1 to 6 substituents selected from hydroxy, hydroxyalkyl and alkoxy groups such as hydroxymethyl, 2-hydroxyethyl, 1,1-dimethyl-2-hydroxyethyl, 2-hydroxypropyl, 2,3-dihydroxypropyl, 2-hydroxy-3-methoxypropyl, 2,3,4,5,6-pentahydroxyhexyl, 1,1-bis(hydroxymethyl)ethyl, 2-(2-hydroxyethoxy)ethyl, 2-methoxyethyl, 1-methyl-2-hydroxyethyl, 3-hydroxypropyl, 3-methoxypropyl and 1,1-bis(hydroxymethyl)-2-hydroxyethyl.

Preferably, $R^4$, $R^5$ and $R^6$ are a hydrogen atom, a methyl group and an alkyl group which may have 1 to 3 substituents selected from hydroxy groups and hydroxyalkoxy groups such as 2-hydroxyethyl, 1,1-dimethyl-2-hydroxyethyl, 1,1-bis(hydroxymethyl)ethyl or 2-(2-hydroxyethoxy)ethyl.

The sphingosines of the component (A) preferably include natural sphingosines or natural type sphingosines represented by the following Formula (3) and derivatives thereof (hereinafter referred to as natural type sphingosines):

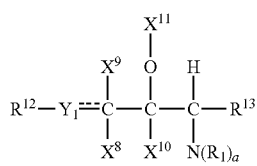

(3)

wherein $R^{12}$ represents a linear, branched or cyclic, saturated or unsaturated hydrocarbon group having 7 to 19 carbon atoms which may be substituted with a hydroxyl group; $Y_1$ represents a methylene group or a methine group; $X^8$, $X^9$ and $X^{10}$ each represent independently a hydrogen atom, a hydroxyl group or an acetoxy group, and $X^{11}$ represents a hydrogen atom or, together with an adjacent oxygen atom, forms an oxo group, wherein when $Y_1$ is a methine group, one of $X^8$ and $X^9$ represents a hydrogen atom, and the other is not present, and when $X^{11}$ forms an oxo group, $X^{10}$ is not present; $R^{13}$ represents a hydroxymethyl group or an acetoxymethyl group; groups "$R_1$"s each are independently a hydrogen atom or an amidino group or each represent independently a linear or branched, saturated or unsaturated hydrocarbon group having in total 1 to 4 carbon atoms which may have a substituent selected from a hydroxyl group, a hydroxyalkoxy group, an alkoxy group and an acetoxy group; "a" represents a number of 2 or 3; and a bond represented by a "broken line and solid line" represents a single bond or a double bond.

In this respect, $R^{12}$ is preferably a linear, branched or cyclic, saturated or unsaturated hydrocarbon group having 7 to 19 carbon atoms, more preferably a linear, saturated or unsaturated hydrocarbon group having 13 to 15 carbon atoms.

Preferably, "a" is preferably 2, and the groups "$R_1$"s each are independently a hydrogen atom or a linear or branched alkyl group having 1 to 4 carbon atoms.

The natural type sphingosines represented by Formula (3) specifically include, natural sphingosines, dihydrosphingosine, phytosphingosine, sphingadienine, dehydrosphingosine, dehydrophytosphingosine and N-alkyl products thereof (for example, N-methyl products).

Either the optically active compounds of a natural type (D(+) compound) or the optically active compounds of a non-natural type (L(−) compound) may be used as these sphingosines, or a mixture of the natural type and the non-natural type may be used. The steric configuration of the compounds described above may be either the steric configuration of the natural type or the steric configuration of the non-natural type or may be a mixture thereof.

Preferred are PHYTOSPHINGOSINE (INCI dictionary; 8th Edition) and compounds represented by the following formulas:

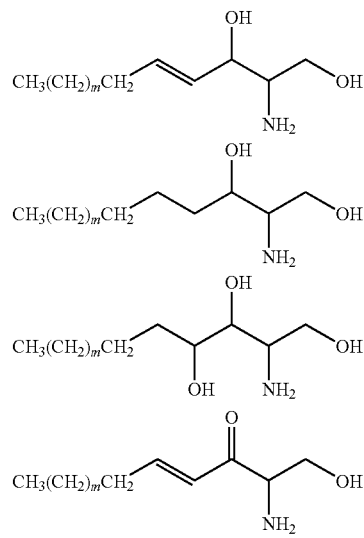

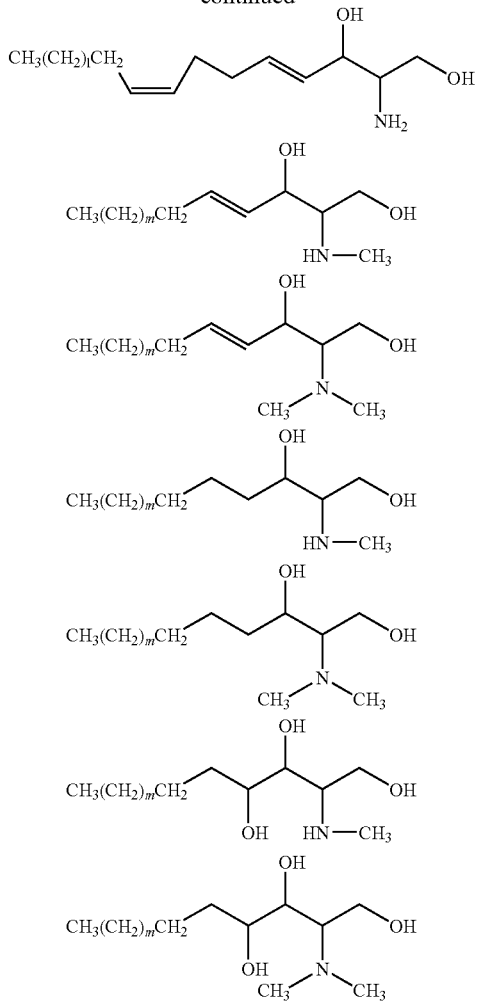

(in the formulas, m represents a number of from 5 to 17, and l represents a number of from 1 to 13).

They may be either extracts obtained from the natural products or synthetic compounds, and commercially available products can be used.

Commercially available natural type sphingosines include, for example, D-Sphingosine (4-Sphingosine) (SIGMA-ALDRICH Co., Ltd.), DS-phytosphingosine (DOOSAN Co., Ltd.) and phytosphingosine (Cosmo Ferm Co., Ltd.).

Further, another type of the sphingosines represented by Formula (1) in the present invention includes a pseudo type (hereinafter referred to as a pseudo type sphingosine) having a structure represented by the following Formula (4):

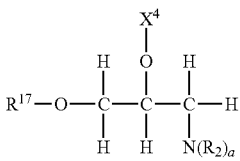

(4)

wherein $R^{17}$ represents a linear, branched or cyclic, saturated or unsaturated hydrocarbon group having 10 to 22 carbon atoms which may be substituted with a hydroxyl group; $X^4$ represents a hydrogen atom, an acetyl group or a glyceryl group; groups "$R_2$"s each represent independently a hydrogen atom or an amidino group or represent a linear or branched, saturated or unsaturated hydrocarbon group having in total 1 to 8 carbon atoms which may have a substituent selected from a hydroxyl group, a hydroxyalkoxy group, an alkoxy group and an acetoxy group; and a represents a number of 2 or 3.

In this respect, $R^{17}$ is preferably an iso-branched alkyl group having 14 to 20 carbon atoms, more preferably isostearyl group. The isostearyl group is still more preferably an isostearyl group in a compound obtained by using as a raw material, isostearyl alcohol originating in a by-product obtained in producing dimer acids using fatty acids originating in animal and vegetable oils.

Further, when a is 2, $R_2$ represents $R^{18}$ and $R^{19}$, and when a is 3, $R_2$ represents $R^{18}$, $R^{19}$ and $R^{20}$.

$R^{18}$, $R^{19}$ and $R^{20}$ include, for example, a hydrogen atom; linear or branched alkyl groups such as methyl, ethyl, propyl, 2-ethylhexyl and isopropyl; alkenyl groups such as vinyl and allyl; an amidino group; and alkyl groups having in total 1 to 8 carbon atoms which have one or more substituents selected from hydroxy, hydroxyalkoxy and alkoxy groups such as hydroxymethyl, 2-hydroxyethyl, 1,1-dimethyl-2-hydroxyethyl, 2-hydroxypropyl, 2,3-dihydroxypropyl, 2-hydroxy-3-methoxypropyl, 2,3,4,5,6-pentahydroxyhexyl, 1,1-bis(hydroxymethyl)ethyl, 2-(2-hydroxyethoxy)ethyl, 2-methoxyethyl, 1-methyl-2-hydroxyethyl, 3-hydroxypropyl, 3-methoxypropyl and 1,1-bis(hydroxymethyl)-2-hydroxyethyl.

Of these, preferred are secondary amines in which one of $R^{18}$ and $R^{19}$ is a hydrogen atom and the other is 2-hydroxyethyl, 1,1-dimethyl-2-hydroxyethyl, 1,1-bis(hydroxymethyl)ethyl or 2-(2-hydroxyethoxy)ethyl.

The pseudo type sphingosines are preferably those in which $R^{17}$ is isostearyl, $X^4$ is a hydrogen atom, $R^{18}$ is a hydrogen atom and $R^{19}$ is an alkyl group having 1 to 3 substituents selected from hydroxy and hydroxyalkoxy groups such as 2-hydroxyethyl, 1,1-bis(hydroxymethyl)ethyl, 1,1-dimethyl-2-hydroxyethyl and 2-(2-hydroxyethoxy)ethyl.

Specific examples of the pseudo type sphingosines include those represented by the following formulas:

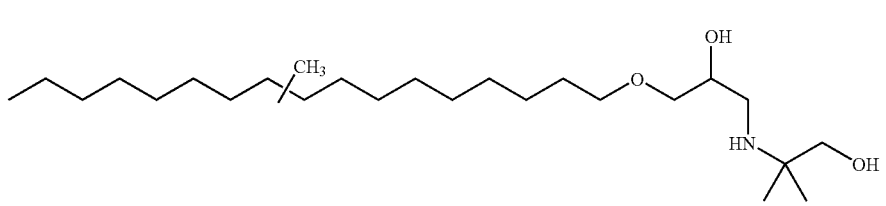

(i)

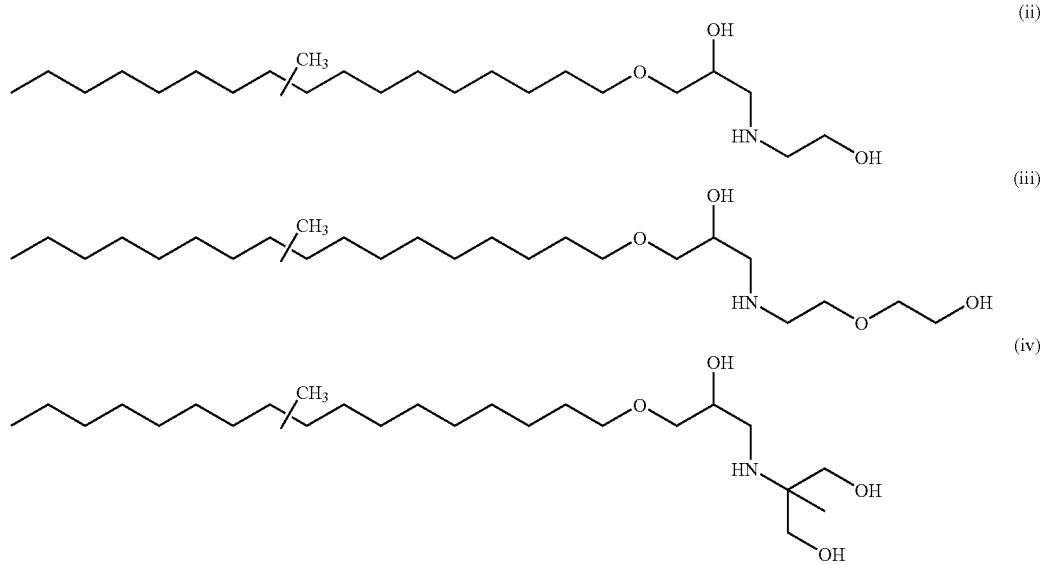

Two or more of the component (A) may be used in combination. A content of the component (A) in the emulsion of the present invention is preferably 0.001 to 10% by weight, more preferably 0.005 to 3% by weight and even more preferably 0.01 to 1.5% by weight.

The acidic compound used as the component (B) in the present invention is selected from inorganic acids and organic acids having a molecular weight of 200 or less. Among them, the inorganic acid includes, for example, phosphoric acid, hydrochloric acid, nitric acid, sulfuric acid, perchloric acid and carbonic acid, with phosphoric acid and hydrochloric acid being more preferred.

The organic acid includes monocarboxylic acids such as formic acid, acetic acid, propionic acid, butyric acid, isobutyric acid and valeric acid; dicarboxylic acids such as succinic acid, phthalic acid, fumaric acid, oxalic acid, malonic acid and glutaric acid; oxycarboxylic acids such as glycolic acid, citric acid, lactic acid, pyruvic acid, malic acid and tartaric acid; and amino acids such as glutamic acid and aspartic acid.

The component (B) is preferably phosphoric acid, hydrochloric acid, succinic acid, citric acid, lactic acid, glutamic acid and aspartic acid, and lactic acid, glutamic acid and aspartic acid are more preferred.

Two or more of the component (B) may be used in combination. A content of the component (B) in the emulsion of the present invention is preferably 0.001 to 10% by weight, more preferably 0.005 to 3% by weight and even more preferably 0.01 to 1.5% by weight.

In order to cationize the amine of the component (A), the component (B) is added preferably in an amount of 0.3 mole or more, more preferably 0.5 to 5 mole and even more preferably 1 to 3 mole per mole of the component (A). For example, an aqueous solution prepared by mixing the component (A) with the component (B) in an equivalent mole has preferably a pH of from 2 to 6 at 25° C. (measured, for example, by means of HORIBA pH METER F-22 after correcting with a phthalate standard solution).

The ceramides used as the component (C) in the present invention is represented by Formula (2) described above, and $R^7$ in the formula is a linear, branched or cyclic, saturated or unsaturated hydrocarbon group having 4 to 30 carbon atoms which may be substituted with a hydroxyl group, a carbonyl group or an amino group, preferably having 7 to 22 carbon atoms which may be substituted with a hydroxyl group.

Z represents any of a methylene group, a methine group and an oxygen atom.

$X^5$, $X^6$ and $X^7$ each represent independently a hydrogen atom, a hydroxyl group or an acetoxy group. It is preferred that zero to one group of $X^5$, $X^6$ and $X^7$ is a hydroxyl group and that the remainder is a hydrogen atom. When Z is a methine group, only one of $X^5$ and $X^6$ is a hydrogen atom, and the other is not present. $X^4$ is preferably a hydrogen atom or a glyceryl group.

$R^8$ and $R^9$ represent a hydrogen atom, a hydroxyl group, a hydroxymethyl group or an acetoxymethyl group. Preferred $R^8$ is a hydrogen atom or a hydroxymethyl group, and preferred $R^9$ is a hydrogen atom.

$R^{10}$ represents a linear, branched or cyclic, saturated or unsaturated hydrocarbon group having 5 to 60 carbon atoms which may be substituted with a hydroxyl group, a carbonyl group or an amino group and which may have an ether bond, an ester bond or an amide bond in a principal chain. Preferably, $R^{10}$ includes a linear, branched or cyclic, saturated or unsaturated hydrocarbon group having 5 to 35 carbon atoms which may be substituted with a hydroxyl group or an amino group or a group obtained by subjecting a linear, branched or cyclic, saturated or unsaturated fatty acid having 8 to 22 carbon atoms which may be substituted with a hydroxyl group to ester bonding or amide bonding to the ω-position of the above hydrocarbon group. The fatty acid to be bonded is preferably isostearic acid, 12-hydroxystearic acid or linoleic acid.

$R^{11}$ represents a hydrogen atom or is a linear or branched, saturated or unsaturated hydrocarbon group having in total 1 to 8 carbon atoms which may have a substituent selected from a hydroxyl group, a hydroxyalkoxy group, an alkoxy group and an acetoxy group. Among them, preferred is a hydrogen atom or a hydrocarbon group having in total 1 to 8 carbon atoms which may be substituted with 1 to 3 groups selected from a hydroxyl group, a hydroxyalkoxy group and an alkoxy group. The hydroxyalkoxy group and the alkoxy group have preferably 1 to 7 carbon atoms.

The ceramides as the component (C) are preferably ceramides represented by the following Formula (5) or (6). (I) Natural ceramides or natural type ceramides and derivatives thereof represented by Formula (5) (hereinafter described as natural type ceramides):

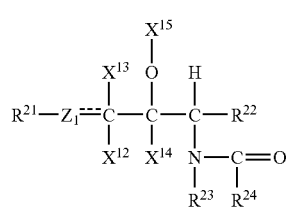

(5)

wherein $R^{21}$ represents a linear, branched or cyclic, saturated or unsaturated hydrocarbon group having 7 to 19 carbon atoms which may be substituted with a hydroxyl group; $Z_1$ represents a methylene group or a methine group; $X^{12}$, $X^{13}$ and $X^{14}$ each represent independently a hydrogen atom, a hydroxyl group or an acetoxy group; $X^{15}$ represents a hydrogen atom or, together with an adjacent oxygen atom, forms an oxo group, wherein when $Z_1$ is a methine group, one of $X^{12}$ and $X^{13}$ is a hydrogen atom, and the other is not present, and when $X^{15}$ forms an oxo group, $X^{14}$ is not present; $R^{22}$ represents a hydroxymethyl group or an acetoxymethyl group; $R^{23}$ represents a hydrogen atom or an alkyl group having 1 to 4 carbon atoms; $R^{24}$ is a linear, branched or cyclic, saturated or unsaturated hydrocarbon group having 5 to 30 carbon atoms which may be substituted with a hydroxyl group or represents a group obtained by subjecting a linear or branched, saturated or unsaturated fatty acid having 8 to 22 carbon atoms which may be substituted with a hydroxyl group to ester bonding to the ω-terminal of the above hydrocarbon group; and a bond represented by a "broken line and solid line" represents a single bond or a double bond.

Preferable is the compound in which $R^{21}$ is a linear alkyl group having 7 to 19 carbon atoms, more preferably 13 to 15 carbon atoms; $Z_1$ is a methine group; one of $X^{12}$ and $X^{13}$ is a hydrogen atom; and $R^{24}$ is a linear alkyl group having 9 to 27 carbon atoms which may be substituted with a hydroxyl group or a linear alkyl group having 9 to 27 carbon atoms to which linoleic acid is ester-bonded. Preferably, $X^{15}$ represents a hydrogen atom or forms an oxo group together with an oxygen atom. $R^{24}$ is more preferably tricocyl, 1-hydroxypentadecyl, 1-hydroxytricocyl, heptadecyl, 1-hydroxyundecyl or nonacocyl in which linoleic acid is ester-bonded to the ω-position.

The specific examples of the natural type ceramides include sphingosine, dihydrosphingosine, phytosphingosine and ceramides Type 1 to 7 obtained by converting sphingadienes to corresponding amides (for example, ceramides of pigs and human beings described in FIG. 2 of J. Lipid Res., 24: 759 (1983) and FIG. 4 of J. Lipid Res., 35: 2069 (1994)).

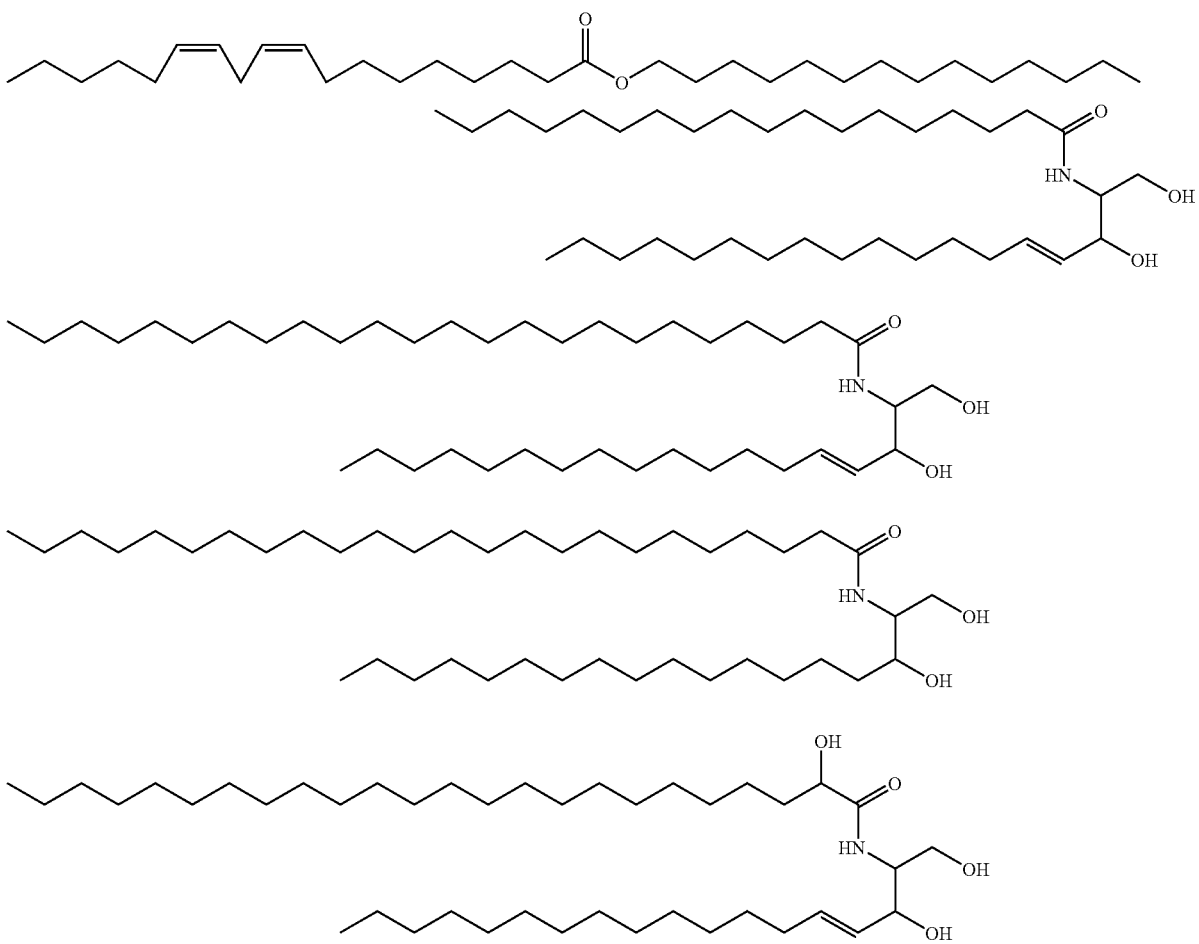

-continued
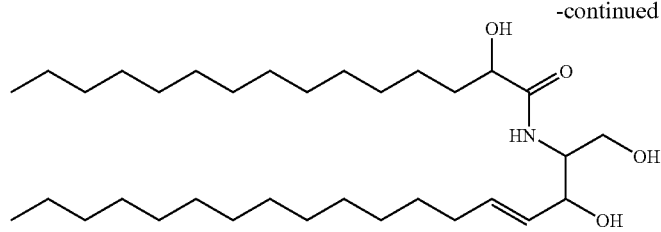
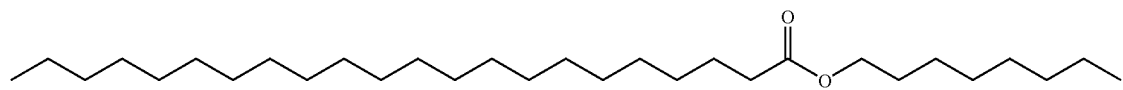
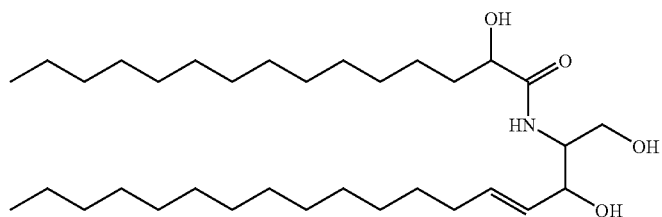
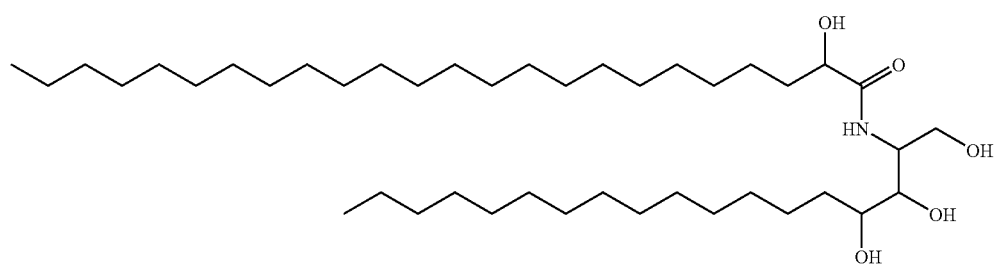
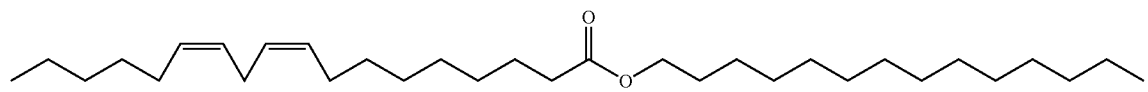
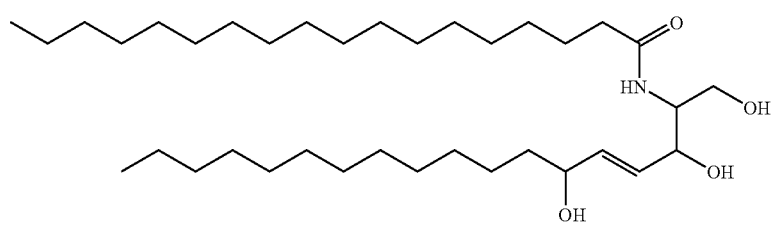
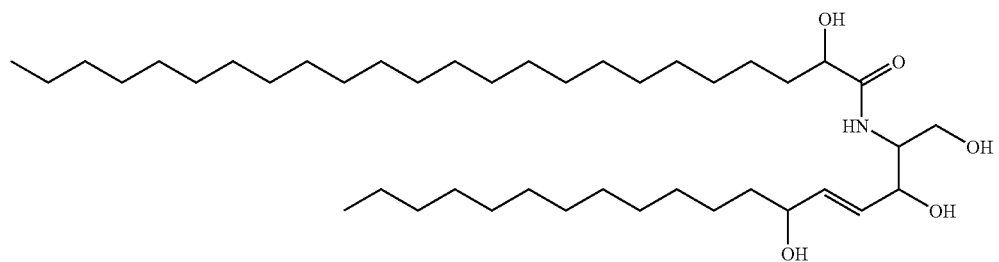
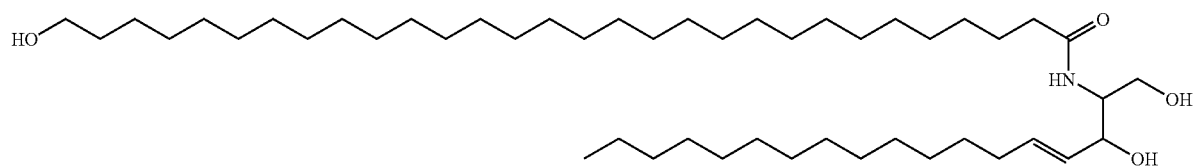

-continued

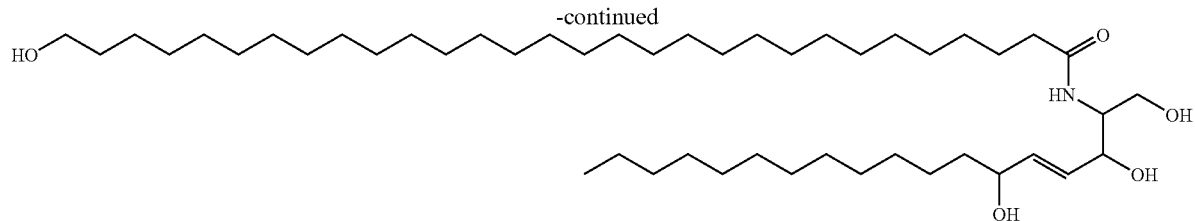

Further, N-alkyl products thereof (for example, N-methyl product) are included therein. They may be either extracts obtained from the natural products or the synthetic compounds, and commercially available products can be used.

Either the optically active compounds of a natural type (D(−)compound) or the optically active compounds of a non-natural type (L(+) compound) may be used for these sphingosines, or a mixture of the natural type and the non-natural type may be used. The steric configuration of the compounds described above may be either the steric configuration of the natural type or the steric configuration of the non-natural type other than the above type or may be a mixture thereof. Preferred are CERAMIDE 1, CERAMIDE 2, CERAMIDE 3, CERAMIDE 5 and CERAMIDE 6II (INCI dictionary; 8th Edition) and compounds represented by the formulas shown below.

The commercially available products of the natural type ceramides include Ceramide I, Ceramide III, Ceramide IIIA, Ceramide IIIB, Ceramide IIIC and Ceramide VI (all manufactured by Cosmo Ferm Co., Ltd.), Ceramide TIC-001 (manufactured by Takasago International Corp.), CERAMIDE II (manufactured by Quest International Co., Ltd.), DS-Ceramide VI, DS-CLA-Phytoceramide, C6-Phytoceramide, DS-Ceramide Y3S (manufactured by DOOSAN Co., Ltd.) and CERAMIDE 2 (manufactured by Sederma Co., Ltd.).

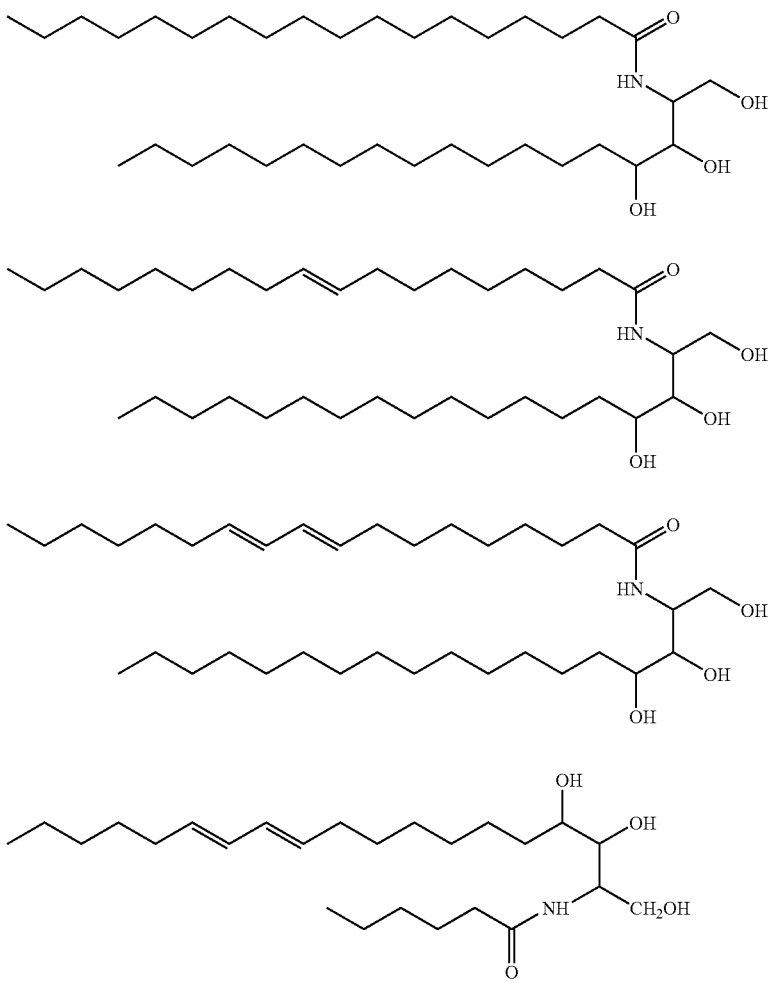

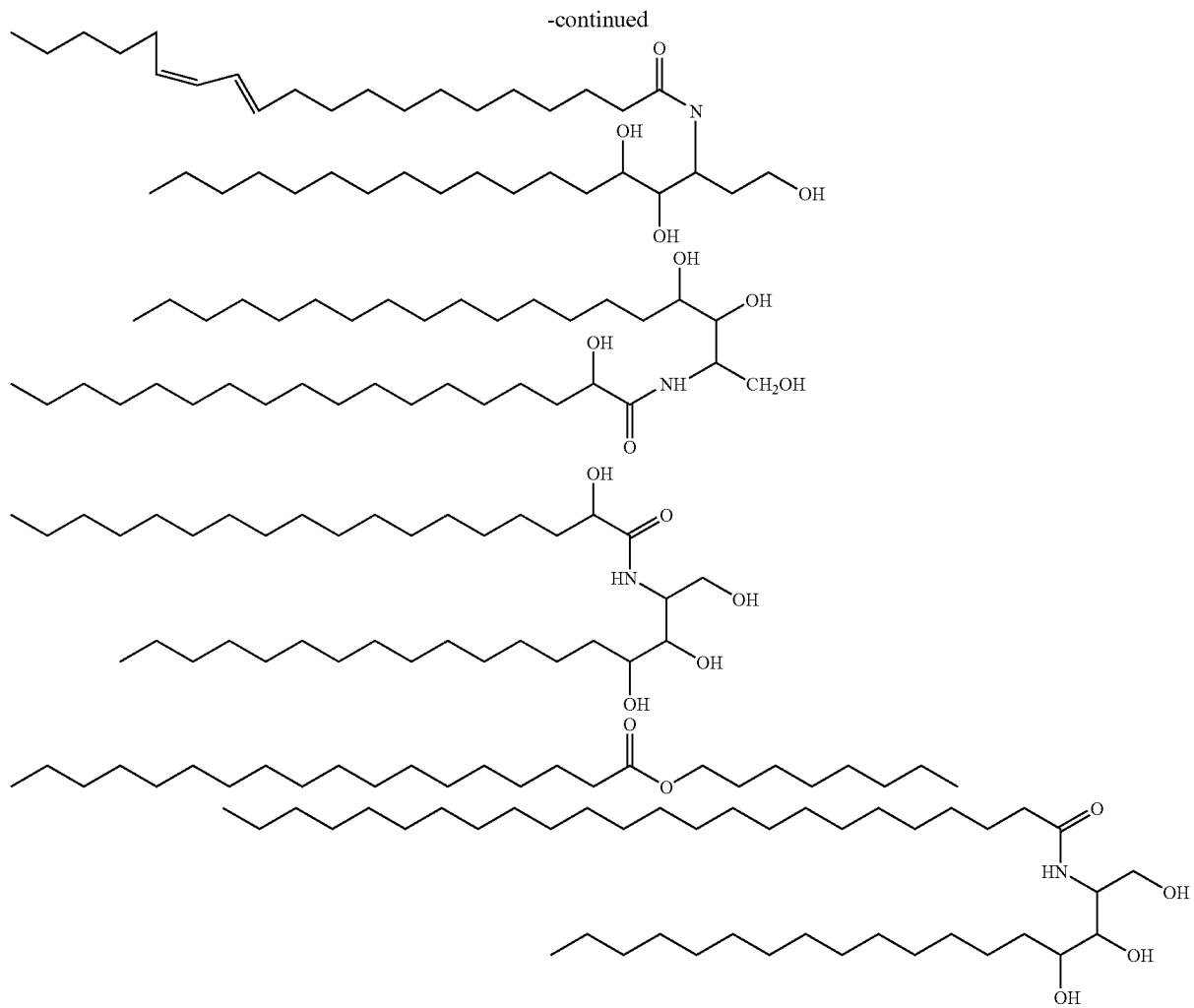

(II) Pseudo type ceramides represented by the following Formula (6):

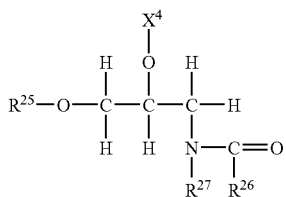

(6)

wherein $R^{25}$ represents a linear, branched or cyclic, saturated or unsaturated hydrocarbon group having 10 to 22 carbon atoms which may be substituted with a hydroxyl group; $X^4$ represents a hydrogen atom, an acetyl group or a glyceryl group; $R^{26}$ represents a linear, branched or cyclic, saturated or unsaturated hydrocarbon group having 5 to 22 carbon atoms which may be substituted with a hydroxyl group or an amino group or a group obtained by subjecting a linear or branched, saturated or unsaturated fatty acid having 8 to 22 carbon atoms which may be substituted with a hydroxyl group to ester bonding to the ω-terminal of the above hydrocarbon group; and $R^{27}$ represents a hydrogen atom or an alkyl group having in total 1 to 8 carbon atoms which may be substituted with a hydroxyl group, a hydroxyalkoxy group, an alkoxy group or an acetoxy group.

$R^{26}$ is preferably nonyl, tridecyl, pentadecyl, undecyl in which linoleic acid is ester-bonded to the ω-position, pentadecyl in which linoleic acid is ester-bonded to the ω-position, pentadecyl in which 12-hydroxystearic acid is ester-bonded to the ω-position or undecyl in which methyl-branched isostearic acid is amide-bonded to the ω-position. The hydroxy alkoxy group or the alkoxy group as $R^{27}$ has preferably 1 to 8 carbon atoms.

Preferred are the pseudo type ceramides represented by Formula (6) in which $R^{25}$ is hexadecyl, $X^4$ is a hydrogen atom, $R^{26}$ is pentadecyl and $R^{27}$ is hydroxyethyl; $R^{25}$ is hexadecyl, $X^4$ is a hydrogen atom, $R^{26}$ is nonyl and $R^{27}$ is hydroxyethyl; or $R^{25}$ is hexadecyl, $X^4$ is glyceryl, $R^{26}$ is tridecyl, $R^{27}$ is 3-methoxypropyl. More preferred is the compound of Formula (6) in which $R^{25}$ is hexadecyl, $X^4$ is a hydrogen atom, $R^{26}$ is pentadecyl and $R^{27}$ is hydroxyethyl.

Two or more of the component (C) may be used in combination. A content of the component (C) in the emulsion of the present invention is preferably 50% by weight or less, more preferably 0.01 to 50% by weight and even more preferably 0.01 to 20% by weight.

In the emulsion of the present invention, a weight proportion ((A)+(B))/(C) of the contents of the components (A), (B) and (C) is preferably 0.0001 or more, more preferably 0.0001 to 1000, even more preferably 0.001 to 100, and still more preferably 0.01 to 10 in terms of the stability.

The ceramide emulsion of the present invention contains neither phospholipid (lecithin) nor an acrylic acid polymer (carboxyl vinyl polymer) in terms of the storage stability.

The ceramide emulsion of the present invention contains water in addition to (A) the sphingosines, (B) the acidic compound and (C) the ceramides. A content of water is preferably 0.1 to 99.99% by weight, more preferably 10 to 99.9% by weight. The whole amount of water may be added in an emulsifying step or only a part thereof may be added in the emulsifying step, and the remaining amount may be added later when cooled down to room temperature.

The ceramide emulsion of the present invention is produced by adding (B) the acidic compound to (A) the sphingosines in emulsifying the ceramides to form the salts of the sphingosines (hereinafter referred to as a sphingosine salt). In this case, a process for producing the ceramides emulsion may be any of (1) a process in which the acidic compound forming a salt with the sphingosines is added to a preliminary mixture of the sphingosines and the ceramides, (2) a process in which the sphingosines are mixed with the acidic compound forming a salt with a sphingosine to form a salt and the ceramides are then added thereto, and (3) a process in which the three components, sphingosines, the acidic compound forming a salt with a sphingosine and the ceramides, are added at the same time. Further, a component isolated as a sphingosine salt may be mixed with the ceramides.

In the present invention, if either the sphingosine or the acidic compound forming a salt with a sphingosine is not present during emulsifying for ceramides, the emulsification can not be achieved. If the emulsification is carried out in the absence of any of the essential components described above and the above short component is added thereafter, the emulsion of the present invention is not obtained.

If both of the sphingosines and the ceramides are solid during emulsification, they can be molten by heating or dissolved in a solvent such as an oil or an alcohol to carry out emulsification. All of the sphingosines and the ceramides which are the raw materials and the sphingosine salts which are reaction products with the acidic compound are preferably liquid.

An emulsifying temperature in producing the ceramides emulsion of the present invention may be any temperature as long as the sphingosines or the ceramides are neither crystallized nor deposited during an emulsifying operation, and it is preferably 120° C. or lower, more preferably 95° C. or lower in terms of an easiness in the work.

In the emulsification, stirring is carried out preferably at 20 to 1000 r/min, more preferably 200 to 1000 r/min and even more preferably 200 to 800 r/min by means of a propeller or the like. Further, it is preferable to conduct additional stirring at 1500 to 10000 r/min, more preferably 4500 to 9000 r/min by means of a homomixer. The emulsifying time is preferably 1 to 20 minutes, more preferably 5 to 20 minutes. When the emulsification is carried out under heating, the emulsion is preferably cooled down to room temperature at a cooling rate of 0.1 to 20° C./min, more preferably 0.1 to 10° C./min, even more preferably 0.1 to 5° C./min.

In producing the ceramide emulsion of the present invention, further addition of a lower alcohol having 1 to 4 carbon atoms and/or a polyhydric alcohol (hereinafter referred to as alcohols) enhances the storage stability and therefore is preferred.

The lower alcohol includes ethyl alcohol. The polyhydric alcohol includes glycerin, sorbitol, propylene glycol, dipropylene glycol, 1,3-butanediol, polyoxyethylene methyl glucoside and polyethylene glycol, and glycerin, 1,3-butanediol, polyoxyethylene methyl glucoside and polyethylene glycol are preferred.

The emulsion is produced preferably by adding the whole amount or a part of these alcohols in the emulsifying step.

Two or more kinds of the alcohols may be used in combination. The alcohols are preferably contained in the emulsion in a proportion of 50% by weight or less, more preferably 0.01 to 20% by weight.

The ceramide emulsion thus produced stays in a transparent, translucent or opaque state. In this case, the terms "transparent" and "translucent" mean that a turbidity (kaoline standard: a turbidity of refined kaoline 1 mg/l liter of water is set to a turbidity of 1 ppm) measured by means of an integrating sphere photoelectric scattering photometer is 1 to 1500 ppm. When a weight ratio ((A)+(B))/(C) of (A) the sphingosines, (B) the acidic compound and (C) the ceramides is 0.2 or more, a transparent or translucent emulsion is obtained, and when it is less than 0.2, an opaque emulsion is obtained. The emulsion is suitably produced so that the oil drop of the emulsion has an average particle diameter in a range of from 3 nm to 200 μm according to the appearance and the uses, and it is preferably 5 nm to 50 μm, more preferably 5 nm to 10 μm in terms of an appearance and a stability of the emulsion. The average particle diameter is measured by means of a dynamic light scattering type particle size distribution measuring apparatus (HORIBA LB-500) or a laser diffraction/scattering type particle size distribution measuring apparatus (HORIBA LA-920).

The ceramide emulsion of the present invention is preferably used as a skin external preparation, for example, a cosmetic, a medicine, a bathing agent, a clean wiping agent or a scalp care agent, and it is more preferably used as a cosmetic. The cosmetic includes skin cosmetics such as a translucent lotion, a translucent emulsion, a moisturizing essence, a whitening essence, a moisturizing emulsion, a moisturizing cream, and the like.

In the case of the skin external preparation, the specific combination of the components (A), (B) and (C) is preferably to combine the component (C) of Formula (5) with the component (A) of Formula (3), or combine the component (C) of Formula (6) with the component (A) of Formula (4). It is more preferred in terms of the stability and the effect to use a compound obtained by substituting a hydrogen atom for $COR^{10}$ bonded to a nitrogen atom in the compound of Formula (2) of the component (C) as the compound of Formula (1) of the component (A).

Further, when the ceramide emulsion is used as a skin external preparation, further containing a higher alcohol, a fluorine oil or silicone into the skin external preparation is preferred, because it enhances the emulsion stability and the use feeling.

The higher alcohol includes stearyl alcohol, cetyl alcohol, isostearyl alcohol, acetic acid lanolin alcohol, acetic acid polyoxyethylene lanolin alcohol, hydrogenated lanolin alcohol, setostearyl alcohol, batyl alcohol, behenyl alcohol and lanolin alcohol. Of these, stearyl alcohol, cetyl alcohol, batyl alcohol and behenyl alcohol are preferred.

Two or more of these higher alcohols may be used in combination. A content of the higher alcohol in the skin external preparation is preferably 10% by weight or less, more preferably 0.01 to 5% by weight.

The fluorine oil includes a compound represented by the following Formula (7):

$$R^{28}-O-(CH_2)_n Rf \qquad (7)$$

wherein $R^{28}$ represents a linear or branched alkyl group having 2 to 30 carbon atoms; n represents an integer of 1 or 2; and Rf represents a linear or branched fuluorocarbon group having 3 to 20 carbon atoms which may have a hydrogen atom at a terminal carbon atom.

In Formula (7), $R^{28}$ is preferably an alkyl group having 6 to 18 carbon atoms and is more preferably hexyl, octyl, decyl and dodecyl.

The group represented by Rf is preferably a fluorine-substituted alkyl group having a chain length of 6 to 12 carbon atoms. It includes, for example, linear or branched perfluoropropyl, perfluorobutyl, perfluoropentyl, perfluorohexyl, perfluoroheptyl, perfluorooctyl, perfluorononyl, perfluorodecyl, perfluoroundecyl, 1,1,2,2,3,3,4,4-octafluorobutyl, 1,1,2,2,3,3,4,4,5,5-decafluoropentyl, 1,1,2,2,3,3,4,4,5,5,6,6-dodecafluorohexyl, 1,1,2,2,3,3,4,4,5,5,6,6,7,7-tetradecafluoroheptyl and 1,1,2,2,3,3,4,4,5,5,6,6,7,7,8,8-hexadecafluorooctyl. Of these, preferred are perfluorohexyl, perfluorooctyl, perfluoroundecyl, 1,1,2,2,3,3,4,4,5,5,6,6-dodecafluorohexyl and 1,1,2,2,3,3,4,4,5,5,6,6,7,7,8,8-hexadecafluorooctyl.

Two or more of the fluorine base oil preparation may be used in combination. A content of the fluorine base oil preparation in the skin external solution is preferably 50% by weight or less, more preferably 0.01 to 10% by weight.

The silicone includes cyclic dimethylpolysiloxanes, chain dimethylpolysiloxanes, high molecular dimethylpolysiloxanes and methylphenylpolysiloxanes, as well as modified silicones such as amino-modified silicones, alkyl-modified silicones, polyether-modified silicones, alcohol-modified silicones and fluorine-modified silicones.

Two or more of the silicone may be used in combination. A content of the silicone in the skin external preparation is preferably 50% by weight or less, more preferably 0.01 to 10% by weight.

In addition to the above components, components used for conventional skin external preparations can suitably be used for the skin external preparation. They include, for example, moisturizers such as glycine betaine, xylitol, trehalose, urea, neutral amino acid and basic amino acid; water-soluble thickeners such as xanthane gum, hydroxyethyl cellulose, methyl cellulose and hydroxypropyl guar gum; oils such as squalane, liquid paraffin, isotridecyl isononanoate, cholesterol, phytosterol, higher fatty acids and cholesteryl isostearate; drug action agents such as allantoin and tocopherol acetate; cationic surfactants such as dimethyldistearylammonium chloride; nonionic surfactants such as polyoxyethylene-hardened castor oil and polyoxyethylene alkyl ethers; organic powders such as cellulose power, nylon powder, cross-linking type silicone powder, cross-linking type methylpolysiloxane powder, porous cellulose powder and porous nylon powder; inorganic powders such as anhydrous silica, zinc oxide and titanium oxide; refrigerants such as menthol and camphor; vegetable extracts; pH buffer agents; antioxidants; UV absorbers; antiseptic agents; perfumes; fungicides; and coloring matters.

In the present invention, a viscosity of the emulsion is influenced by the contents of solid lipids such as ceramides and the other components, the production process and the like. That is, the emulsion of the present invention may be not only a creamy emulsion having a high viscosity but also an emulsion having a low viscosity. For example, even if the viscosity is 1 to 20000 mPa·s at 25° C., deposition of crystals and separation of the emulsion do not occur, and the stability is good. In general, an emulsion having a low viscosity is liable to cause separation by creaming, but according to the present invention, the emulsion having suitable use feeling, spreading and appearance can be obtained in a viscosity falling in a range of 1 to 20000 mPa·s at 25° C.

EXAMPLES

Compounds Used

Pseudo type sphingosine (i); sphingosine of Formula (4), in which $R^{17}$ is isostearyl; $X^4$ is a hydrogen atom; a is 2; $R^{19}$ is 1,1-dimethyl-2-hydroxyethyl; and $R^{18}$ is a hydrogen atom.

Pseudo type sphingosine (ii); sphingosine of Formula (4), in which $R^{17}$ is isostearyl; $X^4$ is a hydrogen atom; a is 2; $R^{18}$ is 2-hydroxyethyl; and $R^{19}$ is a hydrogen atom.

Pseudo type sphingosine (iii); sphingosine of Formula (4), in which $R^{17}$ is isostearyl; $X^4$ is a hydrogen atom; a is 2; $R^{18}$ is 2-(2-hydroxyethoxy)ethyl; and $R^{19}$ is a hydrogen atom.

Pseudo type sphingosine (iv); sphingosine of Formula (4), in which $R^{17}$ is isostearyl; $X^4$ is a hydrogen atom; a is 2; $R^{18}$ is 1,1-bis(hydroxymethyl)ethyl; and $R^{19}$ is a hydrogen atom.

Pseudo type ceramides (i); ceramides of Formula (6), in which $R^{25}$ is hexadecyl; $X^4$ is a hydrogen atom; $R^{26}$ is pentadecyl; and $R^{27}$ is hydroxyethyl.

Pseudo type ceramides (ii); ceramides of Formula (6), in which $R^{25}$ is hexadecyl; $X^4$ is a hydrogen atom; $R^{26}$ is nonyl; and $R^{27}$ is hydroxyethyl.

Example 1

A 100 mL emulsifying bath was charged with 1.0 g of phytosphingosine (melting point: 102 to 107° C., manufactured by Cosmo Ferm Co., Ltd.) to melt it by heating on an oil bath set to 110° C., and 1.0 g of ceramide 2 (melting point: 99 to 105° C., manufactured by Sederma Co., Ltd.) heated in advance to 120° C. was added thereto and the resulting mixture was stirred at 300 r/min for 10 minutes. Then, a mixed solution of 0.2 g of phosphoric acid and 10 g of water was added in one minute while heating the emulsifying bath so that the ceramide was not deposited, and the solution was stirred and emulsified. The emulsion was cooled down to 25° C. at a cooling rate of 1° C./min, and 87.8 g of water was added during cooling to produce a ceramide emulsion.

Example 2

A ceramide emulsion was produced in the same manner and using the same composition as in Example 1 except that the mixed solution of phosphoric acid and water was added before adding ceramide 2.

Example 3

The addition order was changed as described below using the same composition as in Example 1 to produce a ceramide emulsion. Water (10 g) was added to the sphingosine, and the mixture was heated to dissolve the sphingosine. The resulting solution was mixed under stirring with the ceramide 2 which had been molten by heating, and then phosphoric acid was added thereto. The resulting mixture was stirred and emulsified. The remaining amount of water was added in a cooling step.

Example 4

A ceramide emulsion was produced in the same manner as in Example 1 except that an amount of water added to phosphoric acid was changed to 97.8 g (whole amount).

Example 5

A ceramide emulsion was produced in the same manner and using the same composition as in Example 1 except that the ceramides and phosphoric acid were mixed with the sphingosine at the same time and dissolved.

Example 6

A ceramide emulsion was produced in the same manner as in Example 1 except that in Example 1, phosphoric acid was mixed with the sphingosine at the same time and dissolved.

Example 7

A ceramide emulsion was produced in the same manner as in Example 1 except that in Example 1, the sphingosine, the ceramides, phosphoric acid and 10 g of water were mixed at the same time and dissolved.

Example 8

A ceramide emulsion was produced in the same manner as in Example 1 except that in Example 1, the sphingosine and the ceramides were mixed at the same time and dissolved.

Example 9

A ceramide emulsion was produced in the same manner as in Example 1 except that 10 g of glycerin was further added to the sphingosine, the ceramides, phosphoric acid and 10 g of water in the procedure of Example 7, and they were mixed and dissolved at the same time. Incidentally, an amount of water finally added was reduced by the portion of 10 g of glycerin added.

Example 10

A 100 mL emulsifying bath was charged with 1.0 g of phytosphingosine (melting point: 102 to 107° C., manufactured by Cosmo Ferm Co., Ltd.) to melt it by heating on an oil bath set to 110° C., and a mixture of 1.0 g of ceramide 2 heated in advance to 120° C., 1 g of stearyl alcohol, 4 g of dimethylpolysiloxane and 10 g of glycerin was added thereto and stirred at 80° C. at 300 r/min for 10 minutes. Then, a mixed solution of 0.5 g of lactic acid and 10 g of water was added thereto in one minute while heating the emulsifying bath so that crystal was not deposited, and the resulting mixture was stirred and emulsified. Further, the emulsion was stirred at 80° C. at 9000 r/min for 2 minutes by means of a homomixer. Then, the emulsion was cooled down to 25° C. at a cooling rate of 1° C./min, and 72.5 g of water was added during cooling to produce a ceramide emulsion.

Example 11

A ceramide emulsion was produced in the same manner as in Example 10, except that phytosphingosine, ceramide 2, stearyl alcohol, dimethylpolysiloxane and glycerin were mixed and dissolved at the same time in the emulsifying bath.

Example 12

A 100 mL emulsifying bath was charged with 1.0 g of phytosphingosine, 1.0 g of ceramide 2, 1.0 g of stearyl alcohol and 10 g of glycerin to melt them by heating on an oil bath set to 110° C. Then, a mixed solution of 0.5 g of lactic acid and 10 g of water was added thereto in one minute while heating the emulsifying bath so that crystal was not deposited and stirred at 80° C. at 300 r/min for 10 minutes, and 4 g of dimethylpolysiloxane heated in advance to 80° C. was added thereto to emulsify the resulting mixture. Further, the emulsion was stirred at 80° C. at 9000 r/min for 2 minutes by means of a homomixer and then cooled down to 25° C. at a cooling rate of 1° C./min, and 72.5 g of water was added thereto during cooling to produce a ceramide emulsion.

Example 13

Pseudo type sphingosine (ii) (melting point: 45° C.) (1.0 g) was molten by heating to 80° C., and 1.0 g of pseudo type ceramide (i) (melting point: 75° C.) heated in advance to 80° C. was added thereto. The mixture was stirred at 80° C. at 300 r/min for 10 minutes, and then a mixed solution of 0.5 g of L-glutamic acid and 10 g of water was added thereto in one minute while maintaining the emulsifying bath at a temperature of 80° C. and the resulting mixture was stirred to emulsify the mixture. The emulsion was cooled down to 25° C. at a cooling rate of 1° C./min, and 87.5 g of water was added thereto during cooling to produce a ceramide emulsion.

Example 14

Pseudo type sphingosine (ii) (melting point: 45° C.) (1.0 g) was molten by heating to 80° C., and 10.0 g of pseudo type ceramide (i) (melting point: 75° C.) heated in advance to 80° C. was added thereto. The mixture was stirred at 80° C. at 300 r/min for 10 minutes, and then a mixed solution of 0.5 g of L-glutamic acid and 10 g of water was added thereto in one minute while maintaining the emulsifying bath at a temperature of 80° C. and the resulting mixture was stirred to emulsify the mixture. Further, the emulsion was stirred at 80° C. at 9000 r/min for 2 minutes by means of a homomixer and then cooled down to 25° C. at a cooling rate of 1° C./min, and 78.5 g of water was added thereto during cooling to produce a ceramide emulsion.

Example 15

Pseudo type sphingosine (ii) (melting point: 45° C.) (0.1 g) and glycerin (10 g) were molten, and an oil phase component obtained by mixing 5.0 g of pseudo type ceramide (i) (melting point: 75° C.) heated in advance to 80° C., 0.5 g of stearyl alcohol, 0.75 g of cetyl alcohol and 4 g of squalane was added thereto. The mixture was stirred at 80° C. at 300 r/min for 10 minutes, and then a mixed solution of 0.1 g of L-glutamic acid and 10 g of water was added thereto in one minute while maintaining the emulsifying bath at a temperature of 80° C. and the resulting mixture was stirred to emulsify the mixture. Further, the emulsion was stirred at 80° C. at 9000 r/min for 2 minutes by means of a homomixer and then cooled down to 25° C. at a cooling rate of 1° C./min, and 79.55 g of water was added thereto during cooling to produce a ceramide emulsion.

Comparative Example 1

A ceramide emulsion was produced in the same manner as in Example 1 except that phosphoric acid was not used.

Comparative Example 2

Phytosphingosine (1.0 g) was heated and molten in the same manner as in Comparative Example 1, and then 1.0 g of molten ceramide 2 was added thereto and the mixture was stirred at 300 r/min for 10 minutes. The temperature of the emulsifying bath was lowered to 25° C. which was not higher than the melting point of ceramide 2 at a cooling rate of 1° C./min, and then a mixed solution of 0.2 g of phosphoric acid and 87.8 g of water was added thereto to produce a ceramide emulsion.

Comparative Example 3

A ceramide emulsion was produced in the same manner as in Example 1 except that 1 g of lecithin (Egg Yolk Lecithin PL-100P, average molecular weight: 788, manufactured by Kewpie Co., Ltd.) was added together with ceramide 2.

Comparative Example 4

A ceramide emulsion was produced in the same manner as in Example 1 except that 0.2 g of Carbopol 981 (average molecular weight: 1,250,000, manufactured by Goodrich Co., Ltd.) was added together with the remaining amount of water.

Comparative Example 5

A ceramide emulsion was produced in the same manner as in Example 1 except that phytosphingosine was not used. That is, a 100 mL emulsifying bath was charged with 1.0 g of ceramide 2 (manufactured by Sederma Co., Ltd.) to melt it by heating on an oil bath set to 120° C. Then, a mixed solution of 0.2 g of phosphoric acid and 10 g of water was added thereto in one minute while heating the emulsifying bath so that the ceramide was not deposited, and the resulting mixture was stirred and emulsified. The emulsion was cooled down to 25° C. at a cooling rate of 1° C./min, and 88.8 g of water was added thereto during cooling to produce a ceramide emulsion.

The ceramides emulsions prepared in Examples 1 to 15 were left standing still at −5° C., 25° C. and 50° C. for one week to find that ceramides were observed to be neither separated nor deposited in all cases and that they were excellent in emulsion stability. In contrast thereto, ceramides of Comparative Examples 1, 2, 4 and 5 were observed to be separated immediately after production, and stable emulsion systems were not obtained. The emulsion in which ceramides were not separated was obtained in Comparative Example 3, but when it was left standing still at 25° C. for one day, ceramides were coagulated and separated.

Examples 16 to 36

Skin external preparations having compositions shown in Tables 1 to 4 were produced and evaluated for stability.

Production Process

Examples 16 to 19

The components (A) and (C) and the components (7) to (9) were heated to 80 to 120° C. while stirring and molten to prepare oil phases. An aqueous phase obtained by dissolving the component (B) in a part of water of the component (13) by heating was added to the oil phases while stirring (300 r/min). After addition, the resulting mixtures were stirred, if necessary, by means of a homomixer (9000 r/min) and cooled down to 20 to 40° C., and then the components (10) to (13) were added thereto and mixed to obtain skin external preparations.

Examples 20 to 25

The components (A) and (C) and the components (11) to (15) were heated to 80 to 120° C. while stirring and molten to prepare oil phases. Aqueous phases obtained by dissolving the component (B) in a part of water of the component (18) by heating were added to the oil phases while stirring (300 r/min). After addition, the resulting mixtures were stirred, if necessary, by means of the homomixer (9000 r/min) and cooled down to 20 to 40° C., and then the components (16) to (18) were added thereto and mixed to obtain skin external preparations.

Examples 26 to 32

The components (A) and (C) and the components (13) to (23) were heated to 80 to 120° C. while stirring and molten to prepare oil phases. Aqueous phases obtained by dissolving the component (B) in a part of water of the component (31) by heating were added to the oil phases while stirring (300 r/min). After addition, the resulting mixtures were stirred, if necessary, by means of the homomixer (9000 r/min) and cooled down to 20 to 40° C., and then the components (24) to (31) were added and mixed to obtain skin external preparations.

Examples 33 to 36

The components (A) and (C), the components (10) to (15) and (17) were heated to 80 to 120° C. while stirring and molten to prepare oil phases. Aqueous phases obtained by dissolving the component (B) in a part of water of the component (32) by heating were added to the oil phases while stirring (300 r/min). The resulting mixtures were then stirred, if necessary, by means of the homomixer (9000 r/min) and cooled down to 20 to 40° C., and then the components (16) and (18) to (32) were added thereto and mixed to obtain skin external preparations.

Evaluation of Stability:

The appearance was observed with naked eyes after the preparations were left standing still at 50° C., room temperature (25° C.) and −5° C. for one week and judged according to the following criteria:

◯: the stability was good at all temperatures, and neither separation of the emulsion nor deposition was observed.

x: the emulsion was instable at any temperatures, and separation of the emulsion or deposition of crystal was observed.

TABLE 1

| | | Example | | | |
|---|---|---|---|---|---|
| | | 16 | 17 | 18 | 19 |
| | Components (% by weight) | Transparent or translucent emulsion composition of 20000 mPa · s or less | | | |
| A | (1) Phytosphingosine (manufactured by Cosmo Ferm Co., Ltd.) | 0.2 | 0.2 | 0.2 | |
| | (2) Pseudo type sphingosine (i) | | | | 0.2 |
| B | (3) L-glutamic acid | 0.06 | 0.06 | 0.06 | 0.06 |
| C | (4) Pseudo type ceramides (i) | 1 | | | 1 |
| | (5) Ceramide TIC-001 (manufactured by Takasago International Corp.) | | | 1 | |
| | (6) Ceramide type 2 | | 1 | | |

TABLE 1-continued

| | Components (% by weight) | Example 16 | Example 17 | Example 18 | Example 19 |
|---|---|---|---|---|---|
| | | Transparent or translucent emulsion composition of 20000 mPa·s or less | | | |
| Others | (manufactured by Sederma Co., Ltd.) | | | | |
| | (7) Perfluorohexylethyl-1,3-methyl butyl ether (compound described in Japanese Patent Application Laid-Open No. 322563/1999) | | 0.02 | | |
| | (8) Glycerin | 5 | 5 | 4 | 9 |
| | (9) Polyethylene glycol | | | | 1 |
| | (10) 55% ethyl alcohol | | | 1 | |
| | (11) Polyoxyethylene (20) - hardened castor oil | | | | 0.2 |
| | (12) Methylparabene | | | | 0.2 |
| | (13) Water | Balance | | | |
| Appearance | | Translucent | | | |
| Stability | | ○ | ○ | ○ | ○ |
| pH | | 4.5 | 4.5 | 4.5 | 4.5 |

TABLE 2

| | Components (% by weight) | Example 20 | Example 21 | Example 22 | Example 23 | Example 24 | Example 25 |
|---|---|---|---|---|---|---|---|
| | | Emulsion composition of 20000 mPa·s or less | | | | | |
| A | (1) Phytosphingosine (manufactured by Cosmo Ferm Co., Ltd.) | 0.4 | 0.1 | | | | 0.1 |
| | (2) Sphingosine (Formula (6)) | | | 0.1 | | | |
| | (3) Pseudo type sphingosine (i) | | | | 0.1 | | |
| | (4) Pseudo type sphingosine (ii) | | | | | 0.1 | |
| B | (5) Succinic acid | | | | 0.03 | 0.03 | |
| | (6) Phosphoric acid | 0.08 | | | | | |
| | (7) L-glutamic acid | | 0.04 | | | 0.04 | 0.04 |
| C | (8) Pseudo type ceramides (i) | 3 | 4 | 4 | 4 | 4 | |
| | (9) Ceramide type 1 (manufactured by Cosmo Ferm Co., Ltd.) | 0.1 | | | | | |
| | (10) Ceramide type 2 (manufactured by Sederma Co., Ltd.) | | | | | | 4 |
| Others | (11) Stearyl alcohol | | 0.5 | 0.5 | 0.5 | 0.5 | 0.5 |
| | (12) Cetyl alcohol | | 0.5 | 0.5 | 0.5 | 0.5 | 0.5 |
| | (13) Perfluorohexylethyl-1,3-methyl butyl ether (compound described in Japanese Patent Application Laid-Open No. 322563/1999) | | 2 | 2 | 2 | 2 | 2 |
| | (14) Squalane | | 2 | 2 | 2 | 2 | 2 |
| | (15) Glycerin | 9 | 18 | 20 | 20 | 18 | 20 |
| | (16) Polyethylene glycol | | 2 | | | 2 | |
| | (17) 55% ethyl alcohol | 1 | | | | | |
| | (18) Water | Balance | | | | | |
| Appearance | | Opaque | | | | | |
| Stability | | ○ | ○ | ○ | ○ | ○ | ○ |
| pH | | 4.2 | 4.5 | 4.8 | 4.8 | 4.5 | 4.5 |

TABLE 3

| | Component (% by weight) | Example 26 | Example 27 | Example 28 | Example 29 | Example 30 | Example 31 | Example 32 |
|---|---|---|---|---|---|---|---|---|
| | | Emulsion composition of 20000 mPa·s or less | | | | | Emulsion composition of 20000 mPa·s or more | |
| A | (1) Phytosphingosine (manufactured by Cosmo Ferm Co., Ltd.) | | | | | | 0.2 | |
| | (2) Pseudo type sphingosine (i) | | | | | | | 0.2 |
| | (3) Pseudo type sphingosine (ii) | 0.1 | 0.1 | 0.1 | 0.05 | 0.2 | | |
| B | (4) 1N-hydrochloric acid | | | | | 0.6 | | |
| | (5) L-aspartic acid | 0.02 | 0.02 | | | | | |
| | (6) L-glutamic acid | 0.02 | 0.02 | 0.04 | 0.04 | | 0.06 | 0.06 |
| C | (7) Pseudo type ceramides (i) | | | | | | 10 | 5 |
| | (8) Pseudo type ceramides (ii) | | | | | | | 5 |
| | (9) Ceramide type 1 (manufactured by Cosmo Ferm Co., Ltd.) | | | | | | 1 | 1 |

TABLE 3-continued

|  | Component (% by weight) | Example 26 | 27 Emulsion composition of 20000 mPa·s or less | 28 | 29 | 30 | 31 Emulsion composition of 20000 mPa·s or more | 32 |
|---|---|---|---|---|---|---|---|---|
|  | (10) Ceramide type 2 (manufactured by Sederma Co., Ltd.) |  |  | 4 | 4 |  |  | 4 |
|  | (11) Ceramide type 3 (manufactured by Cosmo Ferm Co., Ltd.) | 4 |  |  |  |  | 4 |  |
|  | (12) Ceramide type 6 (manufactured by Cosmo Ferm Co., Ltd.) |  | 4 |  |  |  |  |  |
| Others | (13) Stearyl alcohol | 0.4 | 0.4 | 0.5 | 1 | 1 | 0.5 | 0.5 |
|  | (14) Cetyl alcohol | 0.5 | 0.5 | 0.5 | 1 | 1 | 1 | 1 |
|  | (15) Batyl alcohol | 0.1 | 0.1 |  |  |  |  |  |
|  | (16) Behenyl alcohol |  |  |  | 0.1 |  | 0.5 | 0.5 |
|  | (17) Perfluorohexylethyl-1,3-methyl butyl ether (compound described in Japanese Patent Application Laid-Open No. 322563/1999) | 2 | 2 | 2 |  |  | 4 | 4 |
|  | (18) Perfluoropolyether (FOMBLIN HCO$_4$: manufactured by Montefroth Co., Ltd.) |  |  |  | 4 | 3 |  |  |
|  | (19) Methylpolysiloxane (KF96, 1 cs) |  |  |  |  | 1 |  | 2 |
|  | (20) Cholesterol |  |  | 0.5 |  |  | 1 |  |
|  | (21) Cholesteryl isostearate |  |  |  | 2 | 4 | 4 |  |
|  | (22) Squalane | 2 | 2 | 2 |  | 4 | 2 | 4 |
|  | (23) Glycerin | 20 | 20 | 20 | 10 | 20 | 10 | 10 |
|  | (24) Polyethylene glycol |  |  |  |  | 3 | 3 |  |
|  | (25) 55% ethyl alcohol |  |  |  | 5 |  |  |  |
|  | (26) Polyoxyethylene (20) octyl dodecyl ether |  |  |  | 3 |  |  |  |
|  | (27) Polyoxyethylene (20) lauryl ether sodium sulfate |  |  |  |  |  |  | 0.1 |
|  | (28) Methyl cellulose |  |  |  | 0.5 |  | 0.5 |  |
|  | (29) Guar gum |  |  |  |  | 0.5 |  | 0.5 |
|  | (30) Methylparabene |  |  |  | 0.2 |  |  | 0.2 |
|  | (31) Water |  |  |  | Balance |  |  |  |
| Appearance |  |  |  |  | Opaque |  |  |  |
| Stability |  | ◯ | ◯ | ◯ | ◯ | ◯ | ◯ | ◯ |
| pH |  | 4.5 | 4.5 | 4.5 | 4.8 | 4.0 | 4.8 | 4.8 |

TABLE 4

|  | Component (% by weight) | Example 33 | 34 Emulsion composition of 20000 mPa·s or less | 35 | 36 |
|---|---|---|---|---|---|
| A | (1) Pseudo type sphingosine (ii) | 0.1 | 0.05 |  |  |
|  | (2) Pseudo type sphingosine (iii) |  |  | 0.01 |  |
|  | (3) Pseudo type sphingosine (iv) |  |  | 0.05 | 0.08 |
| B | (4) L-glutamic acid |  | 0.04 |  | 0.02 |
|  | (5) L-aspartic acid | 0.05 |  |  |  |
|  | (6) Lactic acid |  |  | 0.06 | 0.03 |
| C | (7) Pseudo type ceramides (i) |  | 4 | 3 | 3 |
|  | (8) Ceramide type 2 (manufactured by Sederma Co., Ltd.) | 4 |  |  |  |
|  | (9) Ceramide TIC-001 (manufactured by Takasago International Corp.) |  |  | 0.01 | 0.01 |
| Others | (10) Stearyl alcohol | 0.5 | 0.5 | 0.5 | 0.5 |
|  | (11) Cetyl alcohol | 0.5 | 0.75 | 0.75 | 0.75 |
|  | (12) Methylpolysiloxane (KF-96A (10 cs): manufactured by Shin-etsu Chemical Ind. Co., Ltd.) | 4 | 5 | 5 | 5 |
|  | (13) Methylpolysiloxane (KF-96A (1000 cs): manufactured by Shin-etsu Chemical Ind. Co., Ltd.) |  | 1 | 1 | 1 |
|  | (14) Glycerin | 10 | 20 | 20 | 20 |
|  | (15) Polyethylene glycol (PEG1540: manufactured by Sanyo Kasei Ind. Co., Ltd.) |  | 3 | 3 | 3 |
|  | (16) Hydroxypropyl methyl cellulose (Metolose 60SH4000: manufactured by Shin-etsu Chemical Ind. Co., Ltd.) |  | 0.3 | 0.3 | 0.3 |
|  | (17) Cedrol |  | 0.05 | 0.05 | 0.05 |
|  | (18) Japanese linden extract (Falcolex Bodaiju: manufactured by Ichimaru Falcos Co., Ltd. |  | 0.1 |  | 0.05 |
|  | (19) Fucuceae extract (Falcolex Hibamata: manufactured by Ichimaru Falcos Co., Ltd.) |  |  |  | 0.05 |
|  | (20) Witch hazel extract (Hamamerisu Liquid: manufactured by Ichimaru Falcos Co., Ltd.) |  | 0.2 |  |  |

TABLE 4-continued

| Component (% by weight) | Example 33 | 34 | 35 | 36 |
|---|---|---|---|---|
| | Emulsion composition of 20000 mPa·s or less | | | |
| (21) *Althaea officinalis* root extract (Falcolex Arutea: manufactured by Ichimaru Falcos Co., Ltd.) | 0.1 | | | |
| (22) Citron extract (Citron Extract: manufactured by Maruzen Seiyaku Co., Ltd.) | 0.1 | | | |
| (23) *Sanguisorba officinalis* extract (Ju Extract: manufactured by Maruzen Seiyaku Co., Ltd.) | | | | 0.2 |
| (24) Tea extract (Green Tea Liquid: manufactured by Ichimaru Falcos Co., Ltd.) | 0.1 | | | |
| (25) *Phellodendri* Cortex extract (Oubaku Liquid: manufactured by Ichimaru Falcos Co., Ltd.) | | | 0.03 | |
| (26) Royal jelly extract (Royal Jelly Extract: manufactured by Maruzen Seiyaku Co., Ltd.) | | | 0.5 | |
| (27) Glycine betaine (Amino Coat: manufactured by Asahi Kasei Co., Ltd.) | | | | 3 |
| (28) dl-α-Tocopherol acetate (manufactured by Riken Vitamin Co., Ltd.) | | 0.1 | | 0.1 |
| (29) *Eucalyptus* extract (Falcolex Yukari: manufactured by Ichimaru Falcos Co., Ltd.) | | | 0.1 | 0.5 |
| (30) *Thujopsis dolabrata* extract (Asunaro Liquid: manufactured by Ichimaru Falcos Co., Ltd.) | | | 0.5 | 1 |
| (31) Methylparabene | | 0.2 | 0.2 | 0.2 |
| (32) Water | | Balance | | |
| Appearance | | Opaque | | |
| Stability | ○ | ○ | ○ | ○ |
| pH | 4.5 | 4.8 | 4.8 | 4.8 |

All of the skin external preparations of the present invention were excellent in stability.

INDUSTRIAL APPLICABILITY

The ceramide emulsions of the present invention are not separated and deposited even if surfactants are not used, and they are excellent in storage stability. The emulsions having transparent to opaque appearance can readily be obtained by controlling the components.

What is claimed is:

1. A process for production of a ceramide emulsion comprising:
   adding (C) one or more ceramides to (A) one or more sphingosines, and then
   adding (B) an acidic compound and water thereby forming one or more sphingosine salts;
   wherein
   said one or more sphingosine salts emulsify said (C) one or more ceramides thereby forming said ceramide emulsion;
   said (A) one or more sphingosines being represented by Formula (1):

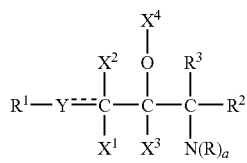

(1)

wherein $R^1$ represents a linear, branched or cyclic, saturated or unsaturated hydrocarbon group having 4 to 30 carbon atoms which is optionally substituted with a hydroxyl group, a carbonyl group or an amino group; Y represents a methylene group, a methine group or an oxygen atom; $X^1$, $X^2$ and $X^3$ each represent independently a hydrogen atom, a hydroxyl group or an acetoxy group, and $X^4$ represents a hydrogen atom, an acetyl group or a glyceryl group or, together with an adjacent oxygen atom, forms an oxo group, wherein when Y is a methine group, either one of $X^1$ and $X^2$ is a hydrogen atom, and the other is not present, and when $X^4$ forms an oxo group, $X^3$ is not present; $R^2$ and $R^3$ each represent independently a hydrogen atom, a hydroxyl group, a hydroxymethyl group or an acetoxymethyl group; groups "R"s each are independently a hydrogen atom or an amidino group or each represent independently a linear or branched, saturated or unsaturated hydrocarbon group having in total 1 to 8 carbon atoms which optionally have a substituent selected from a hydroxyl group, a hydroxyalkoxy group, an alkoxy group and an acetoxy group; "a" represents a number of 2 or 3; and a bond represented by a "broken line and solid line" represents a single bond or a double bond;

said (B) acidic compound being selected from inorganic acids and organic acids having a molecular weight of 200 or less; and said (C) one or more ceramides being represented by Formula (2):

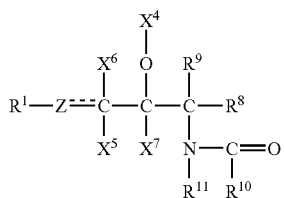

(2)

wherein $R^7$ represents a linear, branched or cyclic, saturated or unsaturated hydrocarbon group having 4 to 30 carbon atoms which is optionally substituted with a hydroxyl group, a carbonyl group or an amino group; Z represents a methylene group, a methine group or an oxygen atom; $X^5$, $X^6$ and $X^7$ each represent independently a hydrogen atom, a hydroxyl group or an acetoxy group, and $X^4$ represents a hydrogen atom, an acetyl group or a glyceryl group or, together with an adjacent oxygen atom, forms an oxo group, wherein when Z is a methine group, one of $X^5$ and $X^6$ is a hydrogen atom, and the other is not present, and when $X^4$ forms an oxo group, $X^7$ is not present; $R^8$ and $R^9$ each represent independently a hydrogen atom, a hydroxyl group, a hydroxymethyl group or an acetoxymethyl group; $R^{10}$ represents a linear, branched or cyclic, saturated or unsaturated hydrocarbon group having 5 to 60 carbon atoms which is optionally substituted with a hydroxyl group, a carbonyl group or an amino group and which optionally have an ether bond, an ester bond or an amide bond in a principal chain; $R^{11}$ represents a hydrogen atom or a linear or branched, saturated or unsaturated hydrocarbon group having in total 1 to 8 carbon atoms which optionally have a substituent selected from a hydroxyl group, a hydroxyalkoxy group, an alkoxy group and an acetoxy group; and a bond represented by a "broken line and solid line" represents a single bond or a double bond.

2. The process according to claim 1, wherein (B) the acidic compound is at least one selected from the group consisting of phosphoric acid, hydrochloric acid, succinic acid, citric acid, lactic acid, glutamic acid and aspartic acid.

3. The process according to claim 1, wherein (B) the acidic compound is present in an amount of from 0.001 to 10% by weight.

4. The process according to claim 1, wherein (C) the one or more ceramides is present in an amount of from 0.01 to 50% by weight.

5. The process according to claim 1, wherein a weight proportion of ((A)+(B))/(C) of (A) is 0.0001 to 1000.

6. The process according to claim 1, wherein emulsification is carried out at a temperature of 120° C. or lower.

7. The process according to claim 1, wherein emulsification is carried out with stirring at 20 to 10000 r/min.

8. The process according to claim 6, wherein after emulsification is carried out at a temperature of 120° C. or lower, the emulsion is cooled to room temperature at a cooling rate of 0.1 to 20° C./min.

9. The process according to claim 1, wherein the ceramide emulsion further comprises at least one selected from the group consisting of a lower alcohol having 1 to 4 carbon atoms and a polyhydric alcohol.

10. The process according to claim 1, wherein the ceramide emulsion further comprises a higher alcohol, a fluorine oil or a silicone oil, said higher alcohol being at least one selected from the group consisting of stearyl alcohol, cetyl alcohol, isostearyl alcohol, acetic acid lanolin alcohol, acetic acid polyoxyethylene lanolin alcohol, hydrogenated lanolin alcohol, setostearyl alcohol, batyl alcohol, behenyl alcohol and lanolin alcohol.

11. The process according to claim 1, wherein the ceramide emulsion has a viscosity of 1 to 20000 mPa·s at 25° C.

* * * * *